(12) United States Patent
Liu et al.

(10) Patent No.: US 7,830,510 B2
(45) Date of Patent: Nov. 9, 2010

(54) APPARATUS FOR HIGH-ACCURACY FIBER COUNTING IN AIR

(75) Inventors: Benjamin Y. H. Liu, North Oaks, MN (US); William D. Dick, Minneapolis, MN (US); Francisco J. Romay, Vadnais Heights, MN (US); Mark J. Battista, White Bear Lake, MN (US); Pedro Lilienfeld, Lexington, MA (US)

(73) Assignee: MSP Corporation, Shoreview, MN (US)

( * ) Notice: Subject to any disclaimer, the term of this patent is extended or adjusted under 35 U.S.C. 154(b) by 13 days.

(21) Appl. No.: 12/364,833

(22) Filed: Feb. 3, 2009

(65) Prior Publication Data
US 2010/0085569 A1    Apr. 8, 2010

Related U.S. Application Data

(60) Provisional application No. 61/103,124, filed on Oct. 6, 2008.

(51) Int. Cl.
*G01N 21/00* (2006.01)

(52) U.S. Cl. .................. 356/338; 356/339

(58) Field of Classification Search .................. 356/337
See application file for complete search history.

(56) References Cited

U.S. PATENT DOCUMENTS

| | | | | | |
|---|---|---|---|---|---|
| 3,692,412 | A | * | 9/1972 | Chubb | 356/338 |
| 4,940,327 | A | * | 7/1990 | Lilienfeld | 356/338 |
| 5,319,575 | A | * | 6/1994 | Lilienfeld | 702/26 |
| 6,005,662 | A | | 12/1999 | Ence | 356/338 |
| 6,512,583 | B1 | | 1/2003 | Ence | 356/338 |

\* cited by examiner

*Primary Examiner*—Roy Punnoose
(74) *Attorney, Agent, or Firm*—Westman, Champlin & Kelly, P.A.

(57) ABSTRACT

The present disclosure has an apparatus for detecting fibers in a gas flowing along a passageway. A laser beam is provided at one end of the passageway and the beam is directed along a length of the passageway through which the gas flows. An electrode system, as disclosed, a quadrupole electrode system is mounted along the passageway to cause fibers carried in the gas to oscillate in a detection zone. A photo detector is positioned laterally of the passageway and detects light scattered by the oscillating fibers and projected through an opening in the passageway to provide an output signal that is a function of the light scattered by the fibers in the detection zone.

13 Claims, 6 Drawing Sheets

APPARATUS FOR HIGH-ACCURACY FIBER COUNTING IN AIR

This application refers to and claims priority on U.S. Provisional Patent application Ser. No. 61/103,124, filed Oct. 6, 2008, and the content of which is incorporated by reference in its entirety.

BACKGROUND OF THE DISCLOSURE

The present disclosure relates to a method and apparatus for counting fibers suspended in air or other gases in order to detect the presence of fibrous material, such as asbestos fiber, other natural and man-made fibers, and the like that may be harmful or injurious to health when inhaled into the lung. While automatic fiber counting devices have been developed (U.S. Pat. No. 4,940,327), there are major shortcomings in the instrument design that have limited their usefulness in the past. The present apparatus is aimed at overcoming the shortcomings of the previous fiber counting devices in order to have a reliable, high accuracy modern instrument for automatic fiber counting in the work place environment.

SUMMARY OF THE DISCLOSURE

The present disclosure relates to an apparatus for automatically and accurately detecting fibers in a gas (air) to determine the concentration of fibers in a selected environment. In one embodiment, as shown, a light source, typically a solid-state, laser light source, provides a substantially parallel beam of light through a flow passageway carrying the flow of gas and fibers. The fibers carried in the gas will scatter light from the laser beam and a photo detector is provided to detect scattered light in a detection zone. An electrode system, preferable a quadrupole electrode system, is provided to produce an oscillating electric field to cause the fibers to oscillate in the detection zone. The flow passageway has a cross-sectional area substantially larger than the cross sectional area of the light beam.

The output of the photo detector is provided to circuitry that provides a pulse train that indicates the concentration of fibers carried in the gas flowing in the passage way. The apparatus disclosed permits counting the fibers accurately and reliably to determine the concentration of fibers in an environment in which workers may be present. Upon detecting a potentially harmful level of airborne fibers, the apparatus may provide a visual or audible alarm to alert workers that respiratory protection devices, such as face masks, may be needed in order to reduce the inhalation hazard of airborne fibers. The apparatus disclosed is capable of operating automatically with minimal attention or intervention by a user.

DESCRIPTION OF THE EMBODIMENTS

Figure 1:
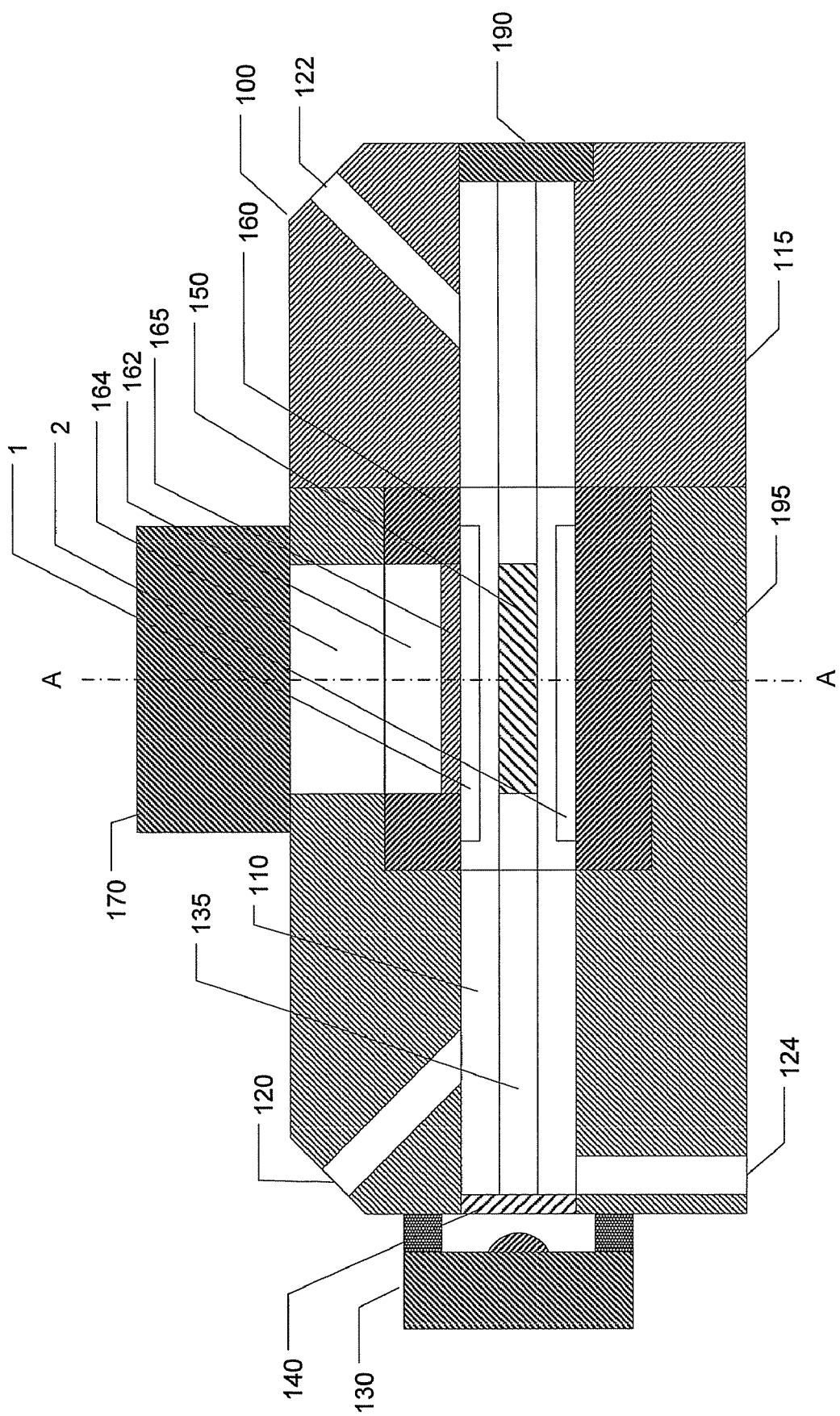
FIG. 1 is a longitudinal sectional view of the fiber detecting module of the present disclosure.

FIG. 1 is a longitudinal sectional view of a fiber detecting module 100 of the present disclosure showing a tubular, cylindrical flow passageway, 110, through which an air (gas) flow carrying suspended fibers passes. Fiber detecting module 100 is provided with an inlet 120 for the sample air flow from a source 200 (FIG. 6) to enter, and an outlet 122 for the air flow to exit. A light source, typically a solid-state laser light source 130 mounted on one end of module 100 projects a beam of light 135 into the cylindrical flow passageway 110. A lens 140 in the path of the laser beam 135 reduces the angular divergence of the beam so that a nearly parallel beam of laser light is projected through the cylindrical flow passageway 110 for fiber detection. Fiber detection occurs within a detection zone 150 in the flow pasageway 110. The detection zone 150 is a portion of the flow passageway formed in a separate cylindrical piece 160, which is a removable sub-assembly inserted into a bore in the body 195 of the module 100, and held in place with a removable end cap portion 115 of the module. The sub-assembly or cylindrical piece 160 includes a quadrupole electrode, and a side opening 162 covered by a window 165. The side opening 162 aligns with an opening 164 in the body 195 to allow light scattered by the fibers in the detection zone to reach a photo detector 170 mounted on the body 195. The window 165 separates the photo detector 170 from the flow passageway 110. Two of the four electrodes in the quadrupole electrode system, indicated at 1 and 2, are visible in the longitudinal sectional view of FIG. 1.

To provide a constant illumination in the detection zone 150, the angular divergence of the laser beam 135 is kept small, typically 2 degrees or less. A light absorbing material 190 is placed at the end of the gas flow passageway 110 to absorb the laser light impinging on the surface and prevent light reflection back into the detection zone 150, which would increase the background light level sensed by the photo detector. An auxiliary clean air inlet 124 is provided so that a small amount of clean, particle free air from a source 210 (FIG. 6) can be introduced into the system to protect lens 140 from being contaminated by fibers and other airborne particulate matter carried by the air flow into the passageway 110 of the system for detection.

The cylindrical piece 160 is designed as a self-contained sub-assembly that can be inserted into the body 195 of the fiber detecting module 100. It is provided with O-ring seals (not shown) to prevent air flow leakage to the surrounding atmosphere. This cylindrical piece contains the quadrupole electrode system, including electrodes 1 and 2, and the window 165 to transmit scattered light from a fiber to the photo detector 170.

Figure 2:
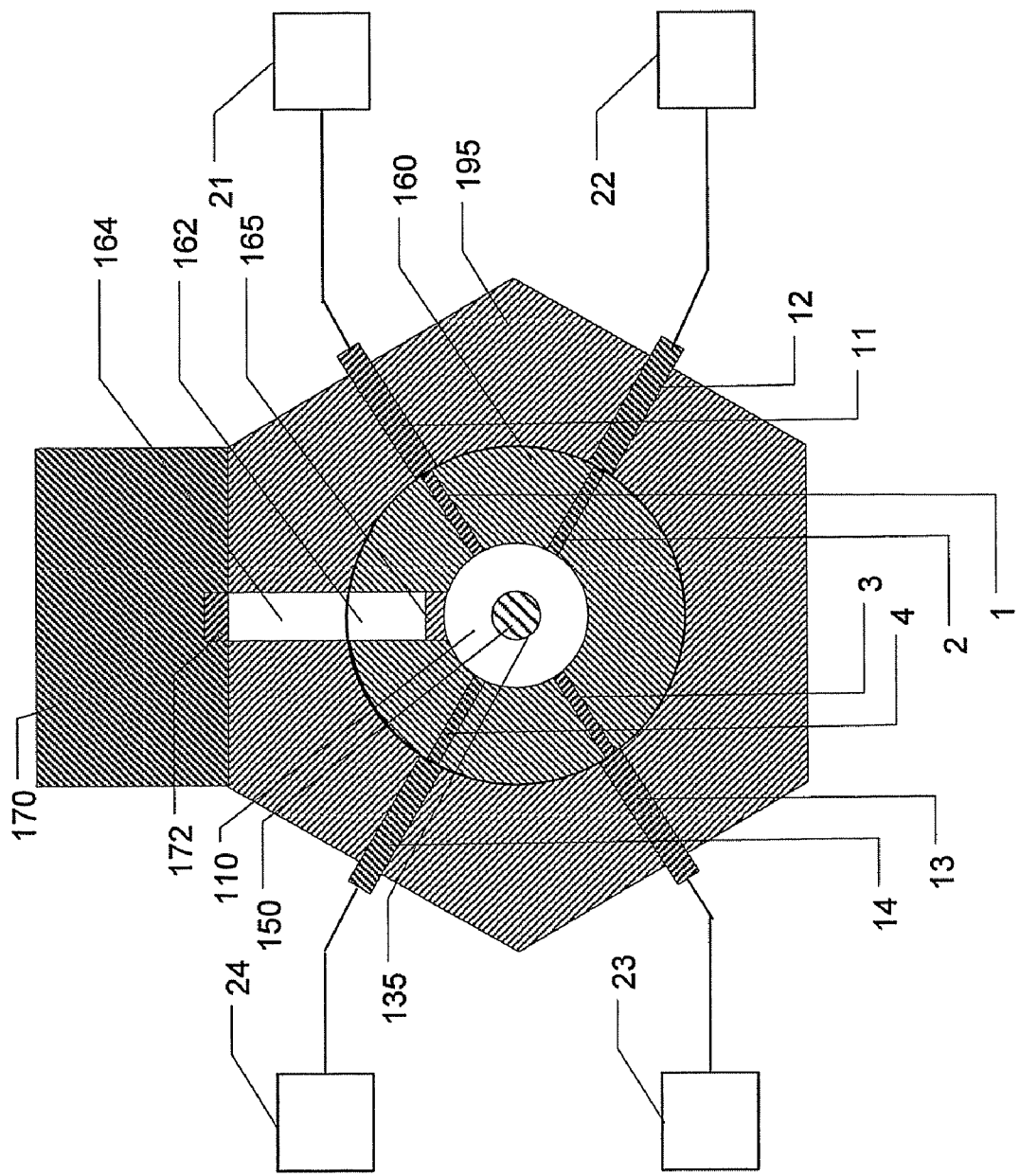
FIG. 2 is a sectional view taken on line A-A in FIG. 1 through the fiber detecting module of FIG. 1 showing a removable sub-assembly carrying a quadrupole electrode and a transparent window.

FIG. 2 is a sectional view taken on line A-A in FIG. 1 through the fiber detection module 100, showing the details of the electrode and the window assembly of the cylindrical piece or sub-assembly 160, the circular cross-section of the flow passageway 110, and the cross-section of the laser beam 135 in the detection zone 150. The laser beam cross section is shown as circular. In practice it can be either circular or elliptical. An elliptical laser cross-section is used in the embodiment of the present disclosure having dimensions of approximately 2.5 mm by 1.5 mm measured along the major and minor axes of the ellipse. The circular cross-section of the flow passageway 110 is approximately 6.0 mm in diameter.

Since the light beam 135 illuminates only a portion of the cross-section of the flow passageway 110, not all fibers carried by the air flow into the flow passageway are illuminated by the light beam, and would thus escape detection by the optical detector system 170. The ratio of the total cross-sectional area A1, of the flow passageway 110, to the cross-sectional area A2 of the light beam 135, which as disclosed is a laser beam, is inversely proportional to the fraction of area of the gas flow passageway 110 that is illuminated by the laser beam 135. An area ratio A1/A2 of 10 means 10% of the gas flow passageway is illuminated by the light beam, while an area ratio A1/A2 of 100 means 1% of the passageway section is illuminated by the light beam 135.

In one embodiment of the apparatus shown, the area ratio, A1/A2, is approximately 10. In comparison, a glass tube electrode system based on the design of U.S. Pat. No. 4,940,327 has an area ratio of approximately 200. This means that the present design has led to an improvement in the area ratio from 200 to 10, thus increasing the illuminated sensing area by a factor of 20. A 20 fold increase in the illuminating sensing area means there is a 20 fold increase in the air flow passing through the illuminated detection zone, bringing 20 fold more fibers for detection and counting. An airborne fiber concentration level that would take an instrument of the older glass tube design 20 minutes to measure can now be measured with the new design in only 1 minute. A measurement time of 60 minutes can now be reduced to 3 minutes. This difference in the detecting and measuring speed is considerable for an instrument that needs to have a fast response to warn the worker of potential hazardous concentration of airborne fibers in the work place. Further reduction in the area ratio is possible. This can be accomplished by decreasing the diameter of the flow passageway, or increasing the cross-sectional area of the light beam, or both. Increasing the light beam cross-section when a laser light source is used may require increasing the output power of the laser so that the illuminating intensity is not greatly reduced in the laser beam. The preferred range for the area ratio, A1/A2, for a practical device is between 2 and 50

The sectional view of FIG. 2 shows the design details of the window-electrode assembly contained in the cylindrical piece 160 of FIG. 1. The body of this cylindrical piece 160 is made of a non-conductive material, preferably a plastic that can be accurately machined. Embedded in the body is the quadrupole electrode system comprised of four electrodes 1, 2, 3 and 4, in the form of narrow strips of metal embedded in the cylindrical plastic block or piece 160. The strips of metal forming the four electrodes extend axially along the flow passageway 110, as shown by electrodes 1 and 2 in FIG. 1. Four separate electrical contacts 11, 12, 13 and 14, are provided to allow an AC or a DC voltage to be applied to the individual electrodes Also embedded in cylindrical block or piece 160 is the narrow transparent window 165, which is made of a high quality precision optical glass to allow light scattered by fibers in the laser illuminated detection zone 150 to pass through and reach the sensing surface 172 of photo-detector 170. Photo-detector 170 can be a photo-diode, or a photomultiplier tube.

The four electrodes shown in FIG. 2 are annularly spaced apart around the passageway. Electrodes 1 and 4 in FIG. 2, are next to each other and on the same side of a longitudinal, axially extending dividing plane of the block 160 bisecting the angle between electrodes 1 and 2. Electrodes 1 and 4 are connected to two separate DC voltage sources 21 and 24, having a positive and negative DC voltage output, respectively. These electrodes with the applied positive and negative voltages will generate a steady DC electric field in the detection zone 150 of module 100 to cause the fiber in the air flowing through the detection zone 150 to become polarized. As a result each fiber will align itself length-wise along the direction of the electric field. In contrast, electrodes 2 and 3 in FIG. 2 are next to each other and on an opposite side of the dividing plane from electrodes 1 and 4. Electrodes 2 and 3 are connected to AC voltage sources 22 and 23, having a positive and negative voltage output, respectively, that varies with time. These varying AC voltages will combine with the DC voltage field from DC sources 21 and 24 to produce an oscillating AC electric field in the detection zone 150. This oscillating AC electric field in turn will cause each fiber to oscillate back and forth in synchronization with the varying AC electric field as the fiber moves through the detection zone. The voltage sources provide excitation for the electrodes.

Figure 3:
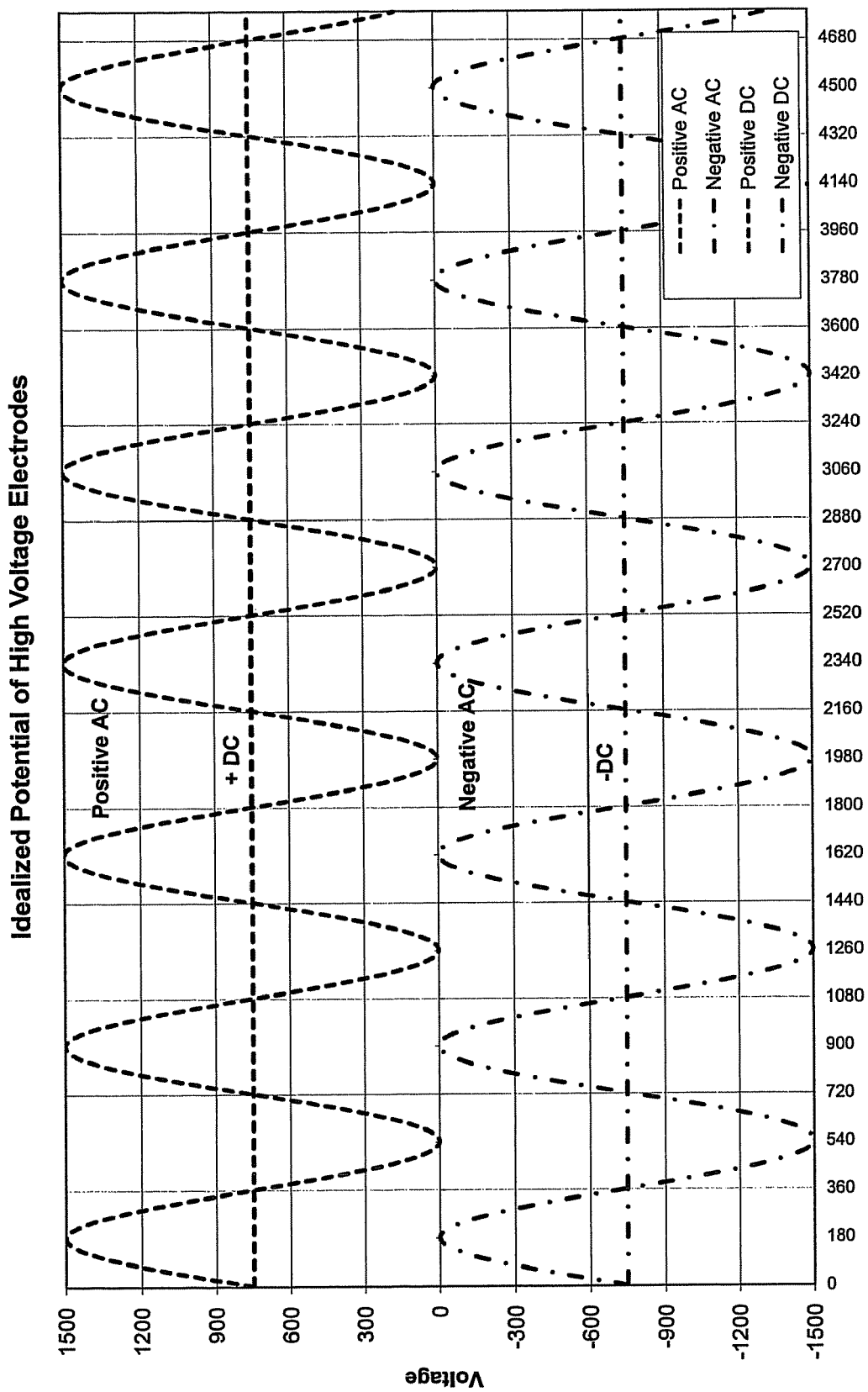
FIG. 3 is a schematic representation of typical voltage wave forms applied to electrodes in a fiber detection zone to orient and oscillate fibers in the detection zone.
Figure 4:
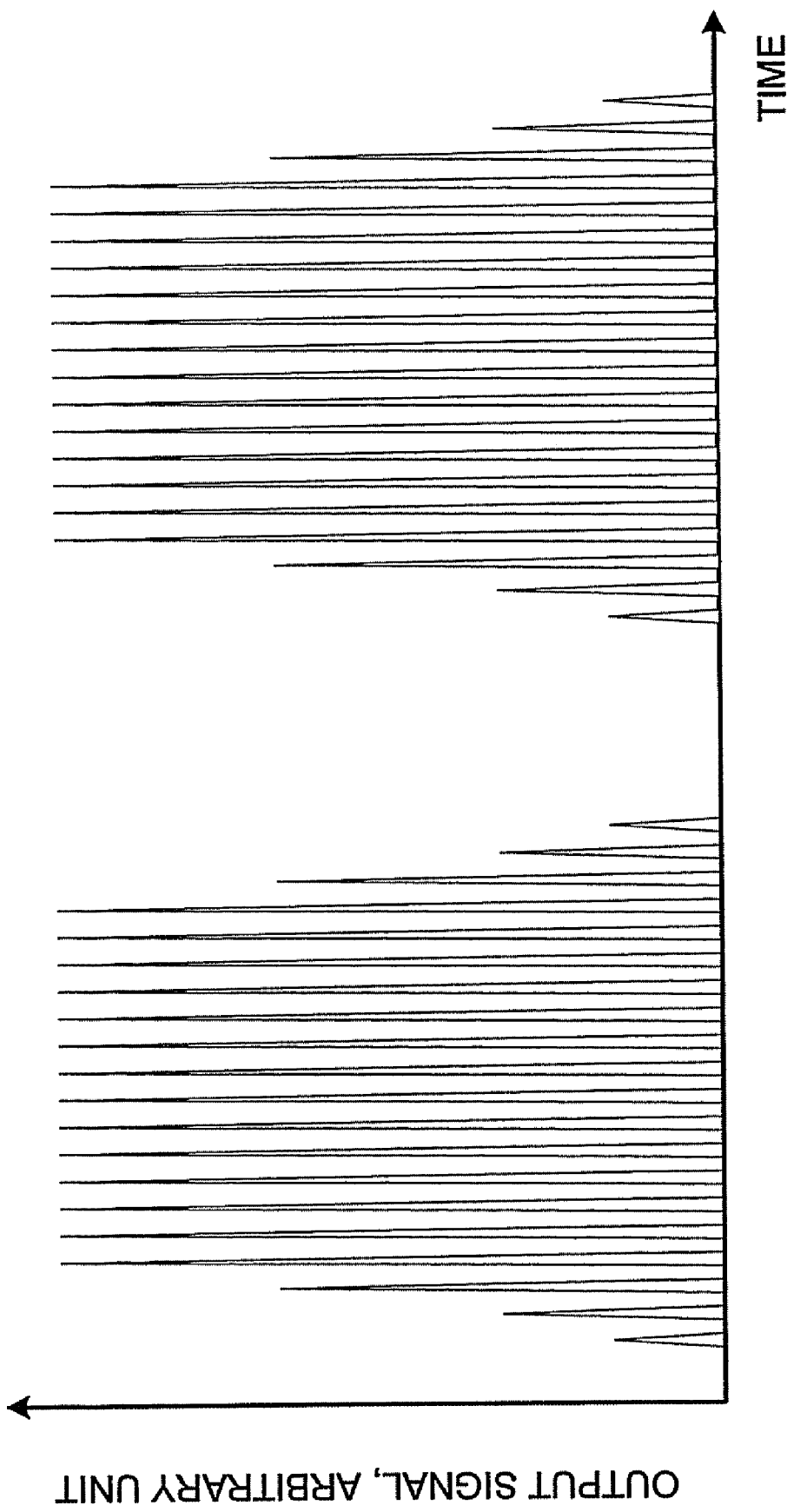
FIG. 4 is a schematic output pulse train from the photo detector from light scattering by an oscillating fiber flowing through an illuminated detecting zone.

In one specific embodiment of the present invention, the DC voltages sources 21 and 24 are provided with 750V DC output of a positive and a negative polarity respectively, while the AC voltage sources 22 and 23 are provided with sinusoidal AC output voltages varying from 0 to +1500V and from 0 to −1500V, respectively. The frequency of the AC voltages is typically 700 Hz. FIG. 3 shows the wave form of the voltages at each electrode and the phase relationship of the positive and negative AC voltages. The quadrupole electrode system with the applied DC and AC voltages shown will cause the fiber to be aligned along the direction of the DC field. At the same time the fiber will oscillate back and forth about 20 times in the estimated 14 milliseconds it takes for the fiber to flow through the detection zone 150. Since light scattering depends on the orientation of the fiber with respect to the optical axis of the photo detector 170, a train of light pulses would arrive at the photo detector to cause the photo detector output to generate a train of voltage pulses as shown in FIG. 4.

Fiber detection consists of analyzing the output of photo detector 170 by appropriate electronic circuitry. Liquid droplets of a spherical shape and mineral dust particles of a compact, but non-spherical shape flowing through the passageway 110 of the system will generate pulses of light varying gradually as the particles flows through the detection zone from one end to the other. In contrast, a fibrous particle in the DC/AC quadrupole electric field will oscillate back and forth at a high rate causing the fiber flowing through the detection zone to scatter a train of light pulses to the photo detector, the light pulses being generated in synchronization with the applied AC electric field. This pulse train can be used to differentiate a fibrous particle from a particle that is of a compact, non-fibrous shape.

Positive identification of fiber and counting the fibers detected require (1) examining the signal to see if there is a pulse train in the scattered light signal and (2) if the individual pulses in the train can be counted reliability to positively identify the pulse train as that from a fibrous particle oscillating in the applied AC quadrupole field, as opposed to pulses resulting from random noise, or spurious signals generated by several particles passing through the detection zone simultaneously. Although all 20 pulses from a pulse train can be counted to identify a fiber, in practice, only a few pulses need to be counted for fiber identification and counting purposes. It has been found counting 10 pulses is more than adequate and as few as 5 pulses can be counted to provide a reliable fiber count. For all practical purposes, counting just 2 pulses to less than 50% of the pulses generated in a pulse train is sufficient for the positive identification of a fiber.

Figure 5:
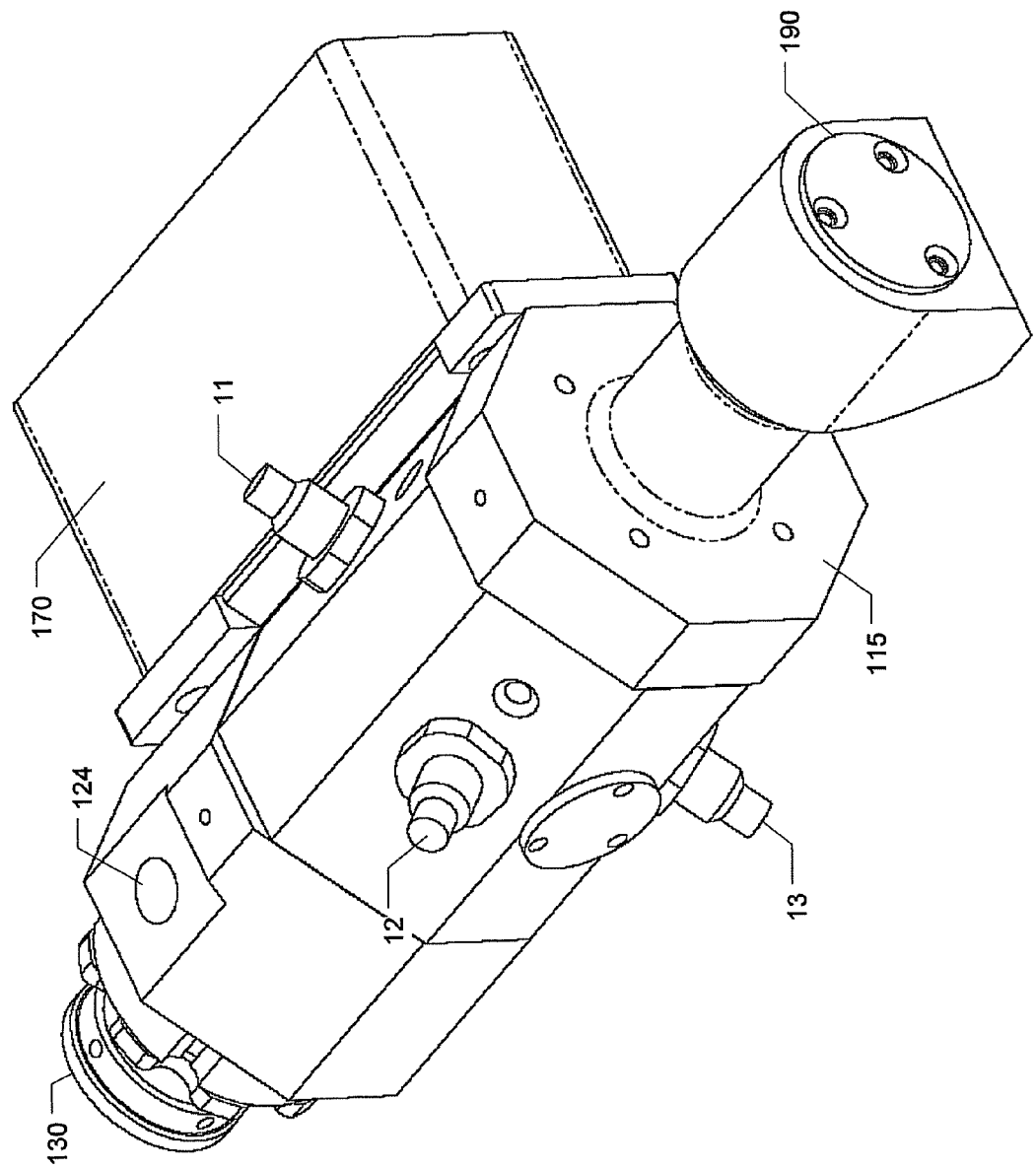
FIG. 5 is a perspective exterior view of the fiber detecting module.

FIG. 5 is 3-dimensional drawing of the fiber detecting module 100 showing the exterior shape of the module. Of the components visible from the outside are the laser light source 130, the clean air inlet 124, the photomultiplier detector 170, electrode terminals 11, 12, and 13, and the light absorber 190.

Figure 6:
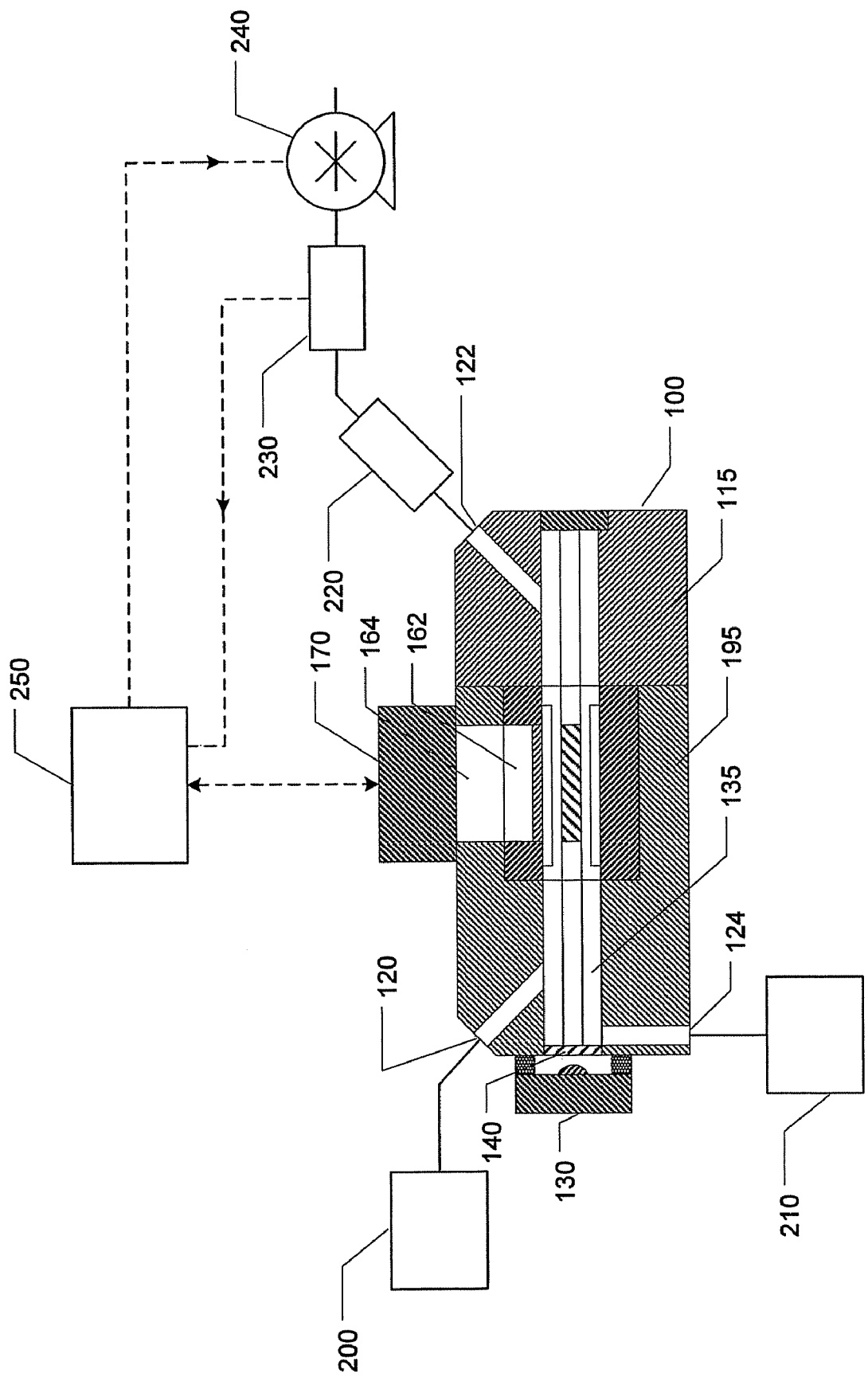
FIG. 6 is a schematic system diagram of the apparatus or system of the present disclosure.

FIG. 6 is a schematic system diagram of the fibrous counting apparatus of the present disclosure. The fiber sensing module 100 is shown with inlet 120 connected to a gas source 200, containing fibers to be counted, and inlet 124 connected to a clean air source 210 to provide clean, particle free air or gas to protect lens 140 from contamination by fibers and particles from source 200. A pump 240 is used to maintain a constant rate of air flow through the system, the flow rate of air through the system is typically 2.0 liter per minute. A filter 220 and a gas flow sensor 230 are placed in the flow path between outlet 122 and pump 240.

Filter 220 is used to collect a fiber sample for subsequent analysis by an independent method. The filter sample can be analyzed to provide a total fiber count, for instance, by optical microscope to confirm that the fibers collected are indeed hazardous asbestos fibers or fibers of a more benign nature. The filter is connected to the outlet 122 of module 100 to minimize the loss of fibers due to deposition on the walls of connecting flow tubing or flow passageways. Filter 220 also removes particles in the gas that may otherwise contaminate the downstream flow components such as flow sensor 230 and pump 240.

As shown in FIG. 6, the fiber counting apparatus of the present disclosure also includes electronic circuitry 250, for signal processing, data collection and various system control and operation functions. Typically circuitry 250 would include one or more electronic circuit boards to provide required DC and AC voltages needed by the quadrupole electrodes, the laser light source 130, the photo-detector 170 and the pump, 240. Sample flow through the system is maintained by pump 240, through feed-back control of the pump speed using the output of flow sensor 230 as a feedback control signal. The pump speed is then adjusted automatically until the feed back signal from the flow sensor agrees with the set-point value desired for the flow Electronic circuitry 250 typically includes a microprocessor based computer so that different system control functions, including the software to carry out certain measurement protocols can be implemented and carried out automatically. The computer is usually provided with graphic user interface to make the device user-friendly and easy to operate. Other features generally found in modern measuring instruments are well known to those skilled in the art of automatic instrument design.

Although the present invention has been described with reference to preferred embodiments, workers skilled in the art will recognize that changes may be made in form and detail without departing from the spirit and scope of the invention.

What is claimed is:

1. An apparatus for detecting fibers in a gas comprising a light source producing a substantially parallel beam of light along a passageway through which said gas flows, a photo detector to detect light scattered from the light beam by a fiber in said gas, said passageway being formed into a separable body piece, an electrode system producing an oscillating electric field to cause said fiber to oscillate, said electrode system having electrodes embedded into an insulating plastic housing forming a subassembly, said subassembly being held in place in said separable body piece, said electrode system comprising a first pair of electrodes open to said passageway on a first side of the passageway coupled to a DC source only, and a second pair of electrodes open to said passageway on a second side of the passageway and spaced from the first pair of electrodes and connected to an AC source only, and said passageway having a cross-sectional area A1, and said beam of light having a cross-sectional area A2, the ratio of said areas, A1/A2, being in the range from 2 to 50.

2. The apparatus of claim 1 further including a filter to collect a sample of fibers suspended in the gas for analysis.

3. The apparatus claim 1 further including a pump, a mechanism to sense the
gas flow through the passageway, and a control mechanism responsive to the mechanism to sense gas flow to vary the speed of the pump to maintain a substantially constant gas flow in said apparatus for measuring the concentration of fibers in said gas.

4. The apparatus of claim 1 further including additionally electronic circuitry to detect and analyze a signal from said photo detector indicating scattered light.

5. An apparatus for detecting fibers in a gas stream flowing along a passageway, a light source producing a substantially parallel beam of light along the passageway to illuminate a portion of the gas stream flowing therethrough, an electrode system comprising a first pair of electrodes positioned on a first side of the passageway and a second pair of electrodes positioned on a side of the passageway opposite from the first side of the passageway, the passageway having a detection zone aligned with the electrodes, the first pair of electrodes being connected to a DC electrical source only and the second pair of electrodes being spaced from the first pair of electrodes and connected to an AC electrical source only to cause a fiber carried in the gas stream to oscillate, a lateral opening in the passageway aligned with the detection zone, and a photo detector receiving light through the lateral opening to provide a signal based on oscillations of a fiber in the detection zone.

6. The apparatus of claim 5 wherein the ratio of the cross sectional area of said passageway and the cross sectional area of said illuminated portion of the gas stream is between 2 and 50.

7. The apparatus of claim 5 and a transparent window mounted in the lateral opening of the passageway, the photo detector being on an opposite side of the window from the passageway.

8. The apparatus of claim 5 wherein the DC
electrical source creates a DC electric field to align the fiber along the direction of the DC field and the AC electrical source creates an electric field to cause the fiber to oscillate back and forth as the fiber moves through the detection zone.

9. The apparatus of claim 5 wherein the light source comprises a laser light source positioned on an exterior end of the passageway, and a lens closing the passageway, the laser projecting light through the lens.

10. A method of detecting fiber suspended in a gas, said method including illuminating fiber suspended in the gas with a beam of light from a light source, providing a detection zone and an electrode system aligned with the detection zone, providing a first pair of electrodes connected to a DC electrical source only on a first side of the detection zone, providing a second pair of electrodes connected to an AC electrical source only spaced from and on an opposite side of the detection zone from the first pair of electrodes, thereby forming a quadrupole oscillating electric field that induces oscillation of fibers illuminated by the beam of light to generate a train of light pulses, detecting light pulse generated in synchronization with the oscillating electrical field with a photo-detector, and counting from two to fewer than 50% of the pulses of each pulse train so detected.

11. The method of claim 10 further comprising providing a flow passageway for the gas, and placing the photo detector laterally of a flow of gas through the flow passageway.

12. The method of claim 10 including positioning the photo detector laterally of the detection zone to receive light scattered by a fiber while in the detection zone.

13. The method of claim 10 wherein the illuminating step comprises illuminating a fiber with a beam of light from a laser light source.

* * * * *